US00PP29801P2

(12) United States Plant Patent
Wood

(10) Patent No.: US PP29,801 P2
(45) Date of Patent: Nov. 6, 2018

(54) ***SYRINGA* PLANT NAMED 'SMNSHBBL'**

(50) Latin Name: ***Syringa* hybrid**
Varietal Denomination: SMNSHBBL

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,483

(22) Filed: Nov. 20, 2017

(51) Int. Cl.
*A01H 5/02* (2018.01)

(52) U.S. Cl.
USPC ..... Plt./248
CPC ..... *A01H 5/02* (2013.01)

(58) Field of Classification Search
USPC ..... Plt./248
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Syringa* cultivar named 'SMNSHBBL' is disclosed, characterized by sweet scented, large, double violet-blue flowers arranged on large panicles. Plants have a good resistance to mildew. The new variety is a *Syringa* normally produced as an outdoor garden or container plant.

2 Drawing Sheets

Latin name of the genus and species: *Syringa* hybrid.
Variety denomination: 'SMNSHBBL'.

BACKGROUND OF THE INVENTION

The present invention comprises a new and distinct variety of *Syringa*, hereinafter referred to by the cultivar name 'SMNSHBBL'. This new *Syringa* was developed through a breeding program in Grand Haven, Mich. The objective of the breeding program was to develop new *Syringa* varieties in a variety of flower colors. 'SMNSHBBL' was selected from a population of seedlings grown from irradiated seed resulting from the crossing of unidentified, unpatented proprietary parents. The crossing date resulting in the new variety is unknown. Selection of the new variety was made during 2007.

The first asexual propagation of 'SMNSHBBL' was carried out during 2010 by softwood cuttings at a commercial nursery in Grand Haven, Mich. 'SMNSHBBL' has been found to retain its distinctive characteristics through successive asexual propagations. Multiple generations have been asexually propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Large double flowers.
2. Large panicles.
3. Strong, pleasant fragrance.
4. Mildew resistance, most likely to *Erysiphe syringae*.

COMPARISON WITH THE PARENT VARIETIES

Parent varieties are unidentified.

COMMERCIAL COMPARISON

'SMNSHBBL' is similar to the commercial variety *Syringa* 'Anabel', unpatented, in most horticultural characteristics. 'SMNSHBBL' however differs in the following:

1. Plants of the new variety produce violet-blue flowers, this comparator produces pink flowers
2. Plants of the new variety are somewhat more compact than plants of this comparator.

DESCRIPTION OF THE PHOTOGRAPHS

This new *Syringa* is illustrated by the accompanying photographs which show the plant's form, foliage and inflorescences. The colors shown are as true as can be reasonably obtained by conventional photographic procedures. Plants were grown in Grand Haven, Mich.

Figure 1:
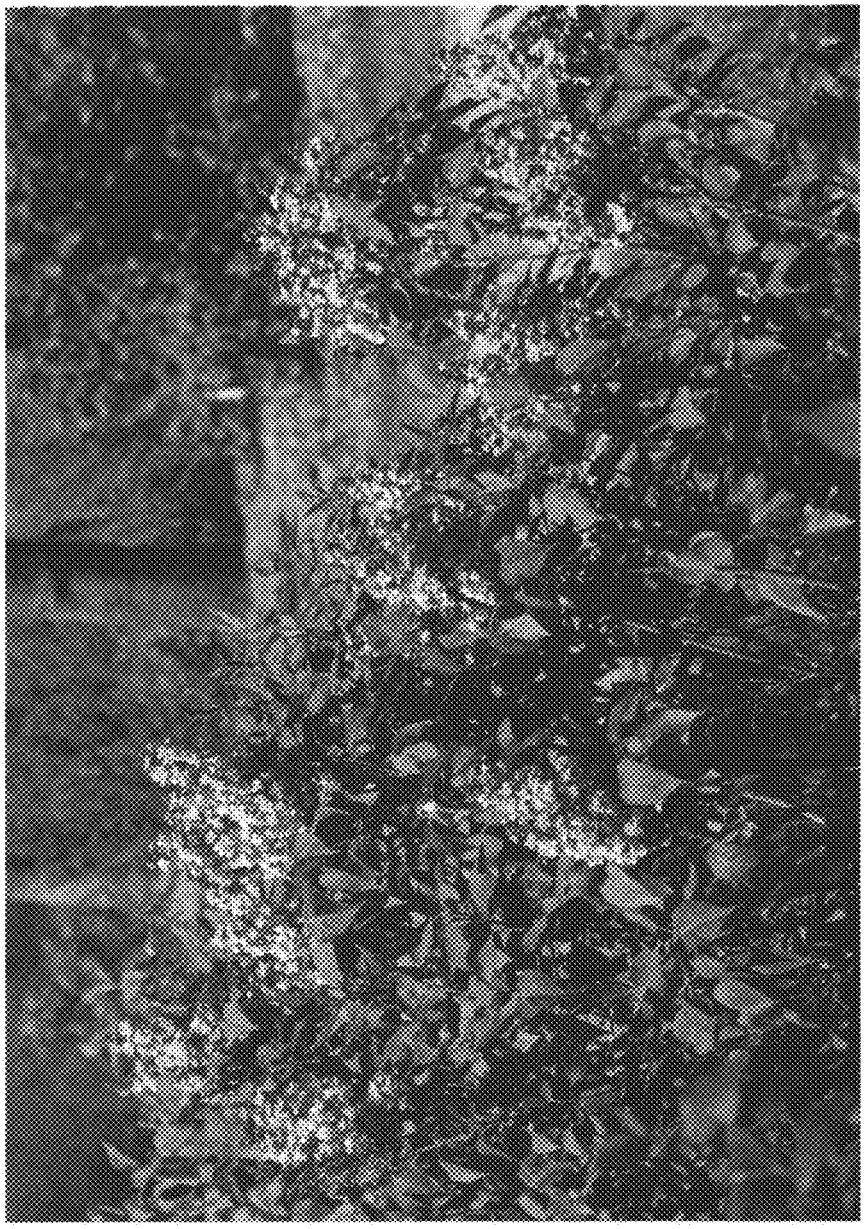

FIG. 1. Shows a flowering plant of 'SMNSHBBL' in the ground at approximately 3 years old during Summer.

Figure 2:
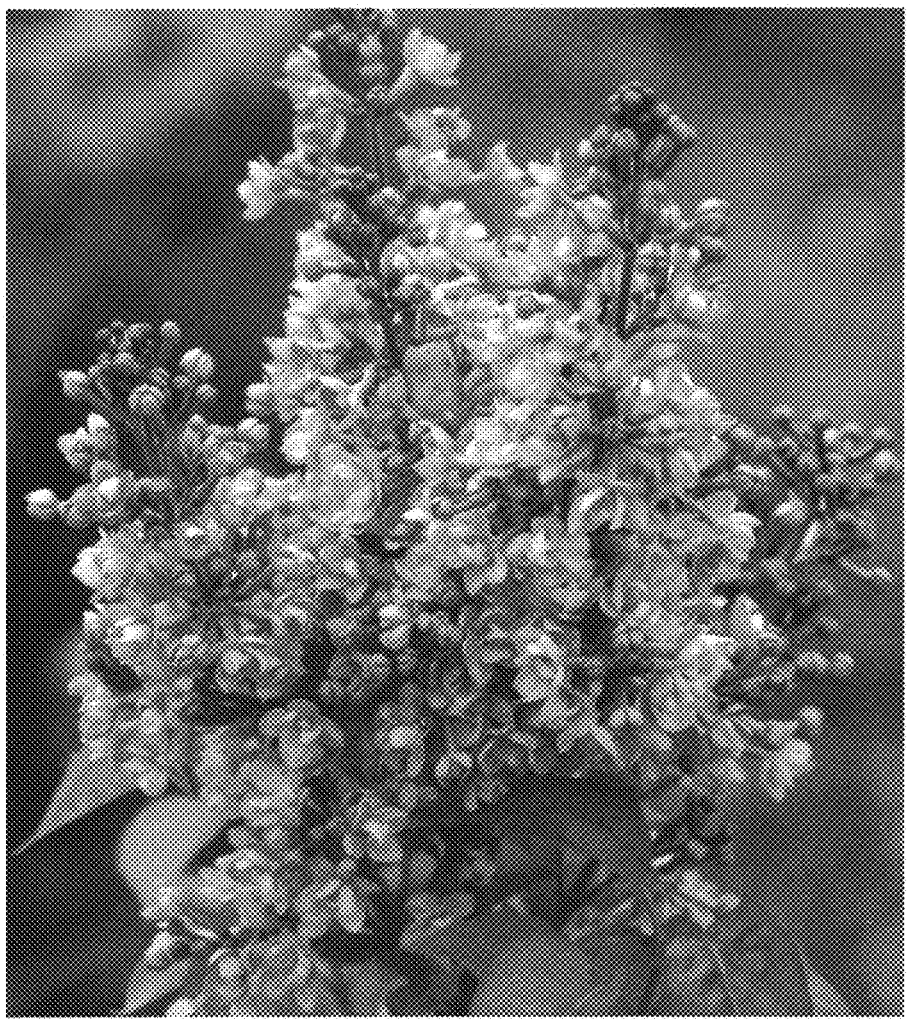

FIG. 2. Shows a close-up view of the inflorescence.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNSHBBL' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Syringa* hybrid 'SMNSHBBL'.
Propagation:

*Typical method*.—Softwood cuttings.

*Time to initiate rooting*.—About 20 days at approximately 18° C. to 27° C.

*Time to produce a rooted young plant*.—About 3 months at approximately 18° C. to 27° C.

*Root description.*—Dense, free branching, thin, fibrous. Colored tan and brown, not accurately measured with an R.H.S. chart.

Plant description:

*Age of plant described.*—About 2 years in a 3 gallon container.

*Growth habit.*—Perennial shrub. Upright and outward.

*Height.*—102 cm in a 3 gallon container.

*Width.*—89 cm in a 3 gallon container.

*Growth rate.*—Moderate.

*Typical commercial container sizes.*—1, 2, and 3 gallon.

Branches:

*Branching habit.*—Upward and some outward.

*Lateral branch quantity.*—Average 15-20.

*Lateral branch length.*—Average 35 cm.

*Lateral branch diameter.*—Average 3.0 mm.

*Branch angle.*—0-90 degrees, mostly 0-30 degrees.

*Branch strength.*—Strong.

*Branch texture.*—Glabrous.

*Branch color.*—Mature Growth: Near Grey-Brown 199C.

*Internode length.*—3.0 cm on average.

Foliage:

*Leaves.*—Persistence: Semi-evergreen. Arrangement: Opposite. Length: Avg. range 8 to 12 cm. Width: Avg. range 7.5 to 11 cm. Shape: Ovate. Apex: Acuminate. Base: Obtuse. Margin: Entire. Texture upper surface: Glabrous. Texture lower surface: Glabrous. Color: Immature: Upper: Near Green 137B. Lower: Near Yellow-Green 144A. Mature: Upper: Near Green 137A. Lower: Near Green 138A. Fall foliage color: Upper: Near Yellow-Green 151A. Lower: Near Yellow-Green 151A.

*Venation.*—Type: Pinnate. Color: Upper: Near Green 143C. Lower: Near Green 143C.

*Petiole.*—Length: Average 2.5 cm. Width: Average 1.5 mm. Texture: Glabrous. Color: New growth upper surface: Near Green 143C. New growth lower surface: Near Green 143C.

Inflorescence:

*Description.*—Double salverform flowers arranged in terminal panicles.

*Flowering season.*—Spring to Mid-Summer.

*Flower longevity.*—2-3 weeks.

*Fragrance.*—Strong, sweet scent.

*Inflorescence per branch.*—Average range 1 to 5.

*Number of flowers per inflorescence.*—120 to 200.

*Inflorescence height.*—Avg. 19.0 cm.

*Inflorescence diameter.*—Avg. 15.0 cm.

*Flowers.*—Flower diameter: 2 cm. Flower depth: 1.8 cm. Flower throat diameter: 3 mm. Flower tube diameter (base): 2 mm. Flower tube length: 1.3 cm. Flower Angle: Upward and outward. Persistent of Self-Cleaning: Self-Cleaning.

*Flower bud.*—Length: 7 mm. Diameter: 1 cm. Shape: Obovate. Color: Near RHS Purple 76B.

*Petals: Number:* 8. Arrangement: Double whorl. Length: Avg. 4 mm. Width: Avg. 3.5 mm. Shape: Elliptical. Apex: Obtuse, cupped. Base: Fused. Margin: Entire. Texture: Glabrous, all surfaces. Color: Immature upper surface: Mostly Violet-Blue 94C with some 98C and White N155C in center. Immature lower surface: Near RHS Purple 76B. Mature upper surface: Mostly Violet-Blue 97A with center colored near White 155A. Mature lower surface: Near RHS Purple 76B. Flower tube (interior): Violet 86B. Flower throat (exterior): Violet 86B.

*Sepals.*—Irregular shapes and sizes. Number: 5. Arrangement: Rotate. Length: About 1 mm. Width: About 1.5 mm. Shape: Triangular. Apex: Acute. Base: Fused. Margin: Entire. Texture: Glabrous upper and lower surfaces. Color: Green 142B, upper and lower surfaces.

*Peduncle.*—Length: Avg. range 7 to 10 cm. Width: Avg. 2.0 mm. Color: Upper section Green 143B. Texture: Glabrous. Angle: About 45°. Strength: Moderate.

*Pedicels.*—Length: Avg. 5 mm. Diameter: Avg. 1.5 mm. Texture: Pubescent. Color: Near RHS Green 143B. Strength: Moderate. Angle: About 45°.

Reproductive organs:

*Gynoecium.*—Pistil number: 1. Pistil length: 3 mm. Stigma shape: Oblong to rounded. Stigma color: Close to White 155A. Style length: about 2 mm. Style color: Close to White 155A.

*Androecium.*—Stamen number: 2. Filament length: 1.5 mm. Filament color: Near Grey 201A. Anther shape: Oblong. Anther length: 2 mm. Anther color: Near Grey 201A. Amount of pollen: Moderate. Pollen color: Near Green-Yellow 1A.

OTHER CHARACTERISTICS

Fruit: Not observed to date.

Seed: Not observed to date.

Disease and insect resistance: Observed resistance to powdery mildew, most likely pathogen is *Erysiphe syringae*. No other significant disease or pest resistance nor susceptibility have been observed.

Temperature range: Observed to tolerate temperatures between −33° C. and 36° C.

What is claimed is:

1. A new and distinct *Syringa* plant named 'SMNSHBBL' as illustrated and described herein.

* * * * *